United States Patent [19]

Inman et al.

[11] Patent Number: 5,444,150

[45] Date of Patent: Aug. 22, 1995

[54] AMINO ACID DERIVATIVE AND BROMOACETYL MODIFIED PEPTIDES FOR THE PREPARATION OF SYNTHETIC PEPTIDE POLYMERS, CONJUGATED PEPTIDES, AND CYCLIC PEPTIDES

[75] Inventors: John K. Inman; Frank A. Robey, both of Bethesda, Md.

[73] Assignee: The United States of America as represented by the Department of Health and Human Services, Washington, D.C.

[21] Appl. No.: 154,786

[22] Filed: Nov. 19, 1993

Related U.S. Application Data

[62] Division of Ser. No. 715,650, Jun. 14, 1991, Pat. No. 5,286,846.

[51] Int. Cl.$^6$ ............... A61K 37/02; C08G 63/48
[52] U.S. Cl. ................... 530/300; 530/317; 530/322; 530/335; 530/336; 530/337; 530/345; 530/350; 530/402; 530/409; 525/54.1; 525/54.11; 528/288; 560/159; 562/450
[58] Field of Search ............... 530/300, 317, 322, 335, 530/336, 337, 345, 350, 402, 409; 525/54.1, 54.11; 528/288; 560/159; 562/450

[56] References Cited

U.S. PATENT DOCUMENTS 5,066,716 11/1991 Robey et al. ............... 525/54.1

OTHER PUBLICATIONS

Robey et al., *Anal. Biochem.*, "Automated Synthesis of N-Bromoacetyl-Modified . . . " vol. 177, pp. 373-377 (1989).

Lindner et al., *Int. J. Peptide Protein Res.*, "Automated synthesis and use of N-chloroacetyl-modified . . . " vol. 30, pp. 794-800 (1987).

Bernatowicz et al., *Analytical Biochemistry*, "Preparation of Peptide-Protein Immunogens . . . " vol. 155, pp. 95-102 (1986).

Kolodny et al., *Analytical Biochemistry*, "Conjugation of Synthetic Peptides to Proteins . . . " vol. 187, pp. 136-140 (1990).

*Primary Examiner*—William H. Beisner
*Assistant Examiner*—Abdel A. Mohamed
*Attorney, Agent, or Firm*—Birch, Stewart, Kolasch & Birch

[57] ABSTRACT

A new amino acid derivative, $N^\alpha$-tert-butoxycarbonyl-$N^\epsilon$-(N-bromoacetyl-$\beta$-alanyl)-L-lysine (BBAL), has been synthesized as a reagent to be used in solid-phase peptide synthesis for introducing a side-chain bromoacetyl group at any desired position in a peptide sequence. The bromoacetyl group subsequently serves as a sulfhydryl-selective cross-linking function for the preparation of cyclic peptides, peptide conjugates and polymers. BBAL residues are stable to final HF deprotection/cleavage. BBAL peptides can be directly coupled to other molecules or surfaces which possess free sulfhydryl groups by forming stable thioether linkages. Peptides containing both BBAL and cysteine residues can be self-coupled to produce either cyclic molecules or linear peptide polymers. Such peptide derivatives are useful in preparing potential peptide immunogens, vaccines and therapeutics, and for substances such as peptides linked to polymers, plastics, enamels and ceramics.

8 Claims, 3 Drawing Sheets

AMINO ACID DERIVATIVE AND BROMOACETYL MODIFIED PEPTIDES FOR THE PREPARATION OF SYNTHETIC PEPTIDE POLYMERS, CONJUGATED PEPTIDES, AND CYCLIC PEPTIDES

This application is a divisional of copending application Ser. No. 07/715,650, filed On Jun. 14, 1991, now U.S. Pat. No. 5,286,846, the entire contents of which are hereby incorporated by reference.

BACKGROUND OF THE INVENTION

1. Field of the Invention

The present invention relates to novel amino acid a derivative, $N^\alpha$-tert-butoxycarbonyl-$N_\epsilon$-(N-bromoacetyl-$\beta$-alanyl)-L-lysine (BBAL), for use in solid-phase or solution-phase peptide synthesis for introducing a side-chain bromoacetyl group at any desired position in a peptide sequence. The bromoacetyl group is subsequently used for the preparation of cyclic peptides, peptide conjugates and peptide polymers. Such peptide derivatives are useful in preparing potential peptide immunogens, vaccines and therapeutics, and for substances such as peptides linked to polymers, plastics, enamels and ceramics.

BACKGROUND OF THE INVENTION

Conjugates of synthetic peptides with proteins, other peptides, polymers (soluble/insoluble; natural/synthetic), and surfaces of special materials are being employed increasingly in biomedical research and biotechnology. Applications of peptide conjugates include the preparation of immunogens (including synthetic vaccines) for raising antibodies to selected portions of protein antigens (Lerner, R. A. (1982) Tapping the immunological repertoire to produce antibodies of predetermined specificity. Nature 299, 592–596; Zavala, F. et al, (1985) Rationale for development of a synthetic vaccine against *Plasmodium falciparum* malaria. Science 228,1436–1440; Tam, J. P. (1988) Synthetic peptide vaccine design: Synthesis and properties of a high-density multiple antigenic peptide system. Proc. Natl. Acad. Sci. U.S.A. 85, 5409–5413; and Milich, D. R. (1989) Synthetic T and B cell recognition sites. Adv. Immunol 45, 195–282), affinity adsorbents, immunoassay components, and cell adhesion surfaces (Massia, S. P. et al, Covalent surface immobilization of Arg-Gly-Asp- and Tyr-Ile-Gly-Ser-Arg-containing peptides (Ser. I.D. No.: 3) to obtain well-defined cell-adhesive substrates. Anal. Biochem. 187, 292–301; and Brandley, B. K. et al, (1988) Covalent attachment of an Arg-Gly-Asp sequence to derivatizable polyacrylamide surfaces: Support of fibroblast adhesion and long-term growth. Anal. Biochem. 172, 270–278).

The locus of attachment of a peptide to its conjugate partner may have a major influence on the desired biological activity or performance of the conjugate (Dyrberg, T. et al, (1986) Peptides as antigens. Importance of Orientation. J. Exp. Med. 164,1344–1349; Schaaper, W. M. M. et al, (1989) Manipulation of antipeptide immune response by varying the coupling of the peptide with the carrier protein. Mol. Immunol. 26, 81–85; and Golvano, J. et al, (1990) Polarity of immunogens: Implications for vaccine design. Eur. J. Immunol. 20, 2363–2366). Strategies for cross-linking a peptide through a single, selected locus are often complicated by the presence of more than one amino or carboxyl group, and the need to protect (then deprotect) amino groups if a carboxyl function is to be activated. Peptides can be more or less selectively derivatized through their N-terminal amino groups by means of acylation reactions in slightly acidic media and/or with use of certain types of reagents, such as, symmetrical anhydrides (10). However, if one wishes to synthesize a peptide in order to prepare a conjugate, planning the synthesis for this purpose can prove very advantageous. For example, some workers have introduced a reactive cysteine residue at the desired position for heteroligation (Green, N. et al, (1982) Immunogenic structure of the influenza virus hemagglutinin. Cell 28, 477–487 and Bernatowicz, M. S. et al, (1986) Preparation of peptide-protein immunogens using N-succinimidyl bromoacetate as a heterobifunctional crosslinking reagent. Anal. Biochem. 155, 95–102); Drijfhout et al completed a sequence on a solid support with an N-terminal S-acetylmercaptoacetyl group (Drijfhout, J. W., Bloemhoff et al, (1990) Solid-phase synthesis and applications of N-(S-acetylmercaptoacetyl) peptides. Anal. Biochem. 187, 349–354). The deprotected peptide was treated with hydroxylamine to remove the S-acetyl group and then joined through its N-terminal sulfhydryl group to a conjugate partner bearing an SH-selective electrophilic function (e.g., an N-substituted maleimide or an $\alpha$-haloacetyl moiety) by means of very stable thioether cross-links (Bernatowicz, M. S. et al (1986), Anal. Biochem. 155, 95–102, supra and Drijfhout, J. W. et al (1990), supra).

Strategy considerations may give preference to placing sulfhydryl groups on the conjugate partner (or using those already present) and coupling it to Cys peptides by means of less stable disulfide bonds. The coupling can be effected through an activating group, such as S-(3-nitro-2-pyridinesulfenyl)(Npys), previously placed on a cysteine side chain (Bernatowicz, M. S. et al, (1986) Preparation of Boc-[S-(3-nitro-2-pyridinesulfenyl)]-cysteine and its use for unsymmetrical disulfide bond formation. Int. J. Peptide Protein Res. 28, 107–112; Drijfhout, J. W. et al, (1988) Controlled peptide-protein conjugation by means of 3-nitro-2-pyridinesulfenyl protection-activation. Int. J. Peptide Protein Res. 32,161–166; and Ponsati, B. et al, (1989) A synthetic strategy for simultaneous purification-conjugation of antigenic peptides. Anal. Biochem. 181, 389–395). A Cys(Npys) residue, introduced in solid-phase peptide synthesis (SPPS), will remain intact during trifluoroacetic acid (TFA) or HF cleavage steps.

For an alternative approach, the peptide synthesis program could be modified in order to introduce an SH-selective electrophile somewhere in the sequence, again allowing use of stable thioether cross-linkages. Lindner and Robey, F. A., (1987) Automated synthesis and use of N-chloroacetyl-modified peptides for the preparation of synthetic peptide polymers and peptide-protein immunogens. Int. J. Peptide Protein Res. 30, 794–800) described the incorporation of N-terminal chloroacetyl-glycylglycyl groups in the last cycle of an automated SPPS. Subsequently, Robey, F. A. and Fields, R. L. (Robey, F. A. et al, (1989) Automated synthesis of N-bromoacetyl-modified peptides for the preparation of synthetic peptide polymers, peptide-protein conjugates, and cyclic peptides. Anal. Biochem. 177, 373–377) and Kolodny, N. and Robey, F. A. (Kolodny, N. et al, (1990) Conjugation of synthetic peptides to proteins: Quantitation from S-carboxymethylcysteine released upon acid hydrolysis. Anal. Biochem. 187, 136–140) described a similar method for introducing the more reactive bromoacetyl group at the N-termini of peptides made by SPPS. The former method is also described in U.S. patent application Serial No. 07/283,849 (filed Dec. 3, 1988). Using this approach, these authors have prepared many useful immunogens either as peptide-protein conjugates or as self-polymers of peptides that contain both a cysteine residue and an N-terminal bromoacetyl group.

The main limitation to the above approach is lack of flexibility in choosing the site for an α-haloacetyl group. To our knowledge, there has not yet been reported a method for introducing an SH-selective alkylating function at any desired position in a peptide that is being synthesized sequentially.

Accordingly, it is desired to obtain a method for introducing a bromoacetyl or chloroacetyl or other haloacetyl or haloacyl cross-linking function at the N- or C-terminus or at any intermediate position of a synthetic peptide that is being prepared.

SUMMARY OF THE INVENTION

Therefore, it is an object of the present invention to provide a peptide synthesis method which may be used to overcome the above-noted limitations.

It is a further object of the present invention to provide an amino acid derivative for introducing the bromoacetyl or other haloacetyl or haloacyl- cross-linking function at the N- or C-terminus or at any intermediate position of a synthetic peptide.

Another object of the present invention is to provide a method for synthesizing the amino acid derivative $N^\alpha$-tert-butoxycarbonyl-$N^3$-(N-bromoacetyl-$\beta$-alanyl)-L-lysine (BBAL).

Still, a further object of the present invention is to provide methods for the preparation of cyclic peptides, peptide conjugates and peptide polymers using BBAL.

Yet a further object of the present invention is to provide methods for synthesizing peptides that have a cross-linking handle at any selected locus for the purpose of preparing peptide-based components of biological activity modifiers, such as immunogens, immunizing epitopes, vaccines and inhibitors, as well as bioassay and affinity separation materials, and medical prostheses.

The foregoing objects and other are accomplished in accordance with the present invention, generally speaking, by providing the amino acid derivative which is a trifunctional compound having (a) haloacetyl or other haloacyl functional group; (b) a free (i.e. un-ionized) carboxyl group, carboxylate salt, carboxylic acid active ester, acyl halide, symmetrical anhydride or mixed anhydride; and (c) a protected primary or secondary amine, wherein the protecting group is removable, for example during a cycle of stepwise synthesis in which this trifunctional compound is being inserted in the desired product, such as for example, $N^\alpha$-tert-butoxycarbonyl-$N^\epsilon$-(N-bromoacetyl-$\beta$-alanyl)-L-lysine (BBAL) as well as a method for synthesizing the same. The present invention further relates to methods for preparing various cyclic peptides, peptide conjugates and peptide polymers using BBAL. The present invention also relates to methods for synthesizing peptides that have a cross-linking handle at any selected locus for the purpose of preparing peptide-based components of biological activity modifiers, bioassay and affinity separation materials, and medical prostheses.

Further scope of the applicability of the present invention will become apparent from the detailed description and drawings provided below. However, it should be understood that the detailed description and specific examples, while indicating preferred embodiments of the invention, are given by way of illustration only, since various changes and modifications within the spirit and scope of the invention will become apparent to those skilled in the art from this detailed description. All of the references cited below are incorporated herein by reference.

BRIEF DESCRIPTION OF THE DRAWINGS

The invention is further illustrated in the accompanying drawings wherein.

DETAILED DESCRIPTION OF THE INVENTION

Figure 1:
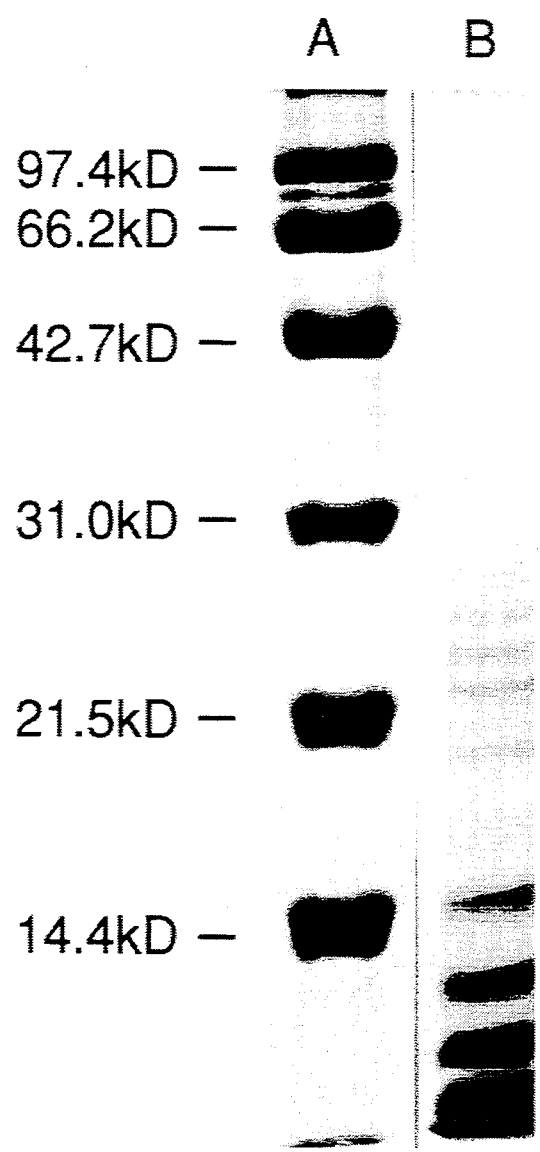
FIG. 1 is a SDS-PAGE run of a peptide polymer obtained by intermolecular cross-linking of a BBAL-containing peptide with itself through a co-existing cysteine residue.

The present invention relates to trifunctional compounds which include (a) a haloacetyl or other halo acyl functional group; (b) a free (i.e. un-ionized) carboxyl group, carboxylate salt, carboxylic acid active ester, acyl halide, symmetrical anhydride or mixed anhydride; and (c) a protected primary or secondary amine, wherein the protecting group is removable. The haloacyl functional group may be acid (acyl) chlorides, acyl bromides or acyl fluorides or possibly acyl iodides, preferably acyl chloride and the haloacetyl group is preferably a bromoacetyl or chloroacetyl group. The trifunctional compound also contains a carboxyl-containing group (b) which may be an acyl halide, a thio ester, and acid anhydride (either a symmetric anhydride or an asymmetric anhydride), any type of ester, a free acid or carboxylate anion. The protected primary or secondary amine (c) is preferably protected with a group that is nonreactive and can be removed by treatment with a substance such as trifluoroacetic acid or a secondary amine such as piperidine. Such protecting groups are preferably tert-butoxycarbonyl (t-BOC) which can be removed for example by treatment with trifluoroacetic acid or 9-fluorenylmethoxy-carbonyl (Fmoc) which can be removed by treatment with a secondary amine such as piperidine.

The present invention further relates to a new Boc-amino acid derivative, $N^\alpha$-tert-butoxycarbonyl-$N^\epsilon$-(N-bromoacetyl-$\beta$-alanyl)-L-lysine (BBAL). With these compounds, one can introduce the bromoacetyl cross-linking function at the N- or C-terminus or at any intermediate position of a synthetic peptide that is being prepared by solution phase methods, or by manual, semi-automated or automated SPPS programs employing temporary $N^\alpha$-Boc protection and final HF-induced deprotection and cleavage. Coupling of these peptides to thiol-bearing or other nucleophile-bearing carriers can be readily accomplished by mixing the components in a neutral or slightly alkaline buffered medium. The ensuing peptide-carrier conjugates may be quantitatively characterized by means of the $\beta$-alanine liberated upon acid hydrolysis of a sample. If co-reactant groups are cysteine sulfhydryls, S-carboxymethylcysteine (CMC) also appears in the hydrolyzate (Kolodny, N. et al, supra). The β-alanine residue places additional spacing in the cross-link and appears to be a necessary part of the structure of BBAL that results in its being a stable solid that can be conveniently stored, weighed and dispensed for synthesizer operations.

The trifunctional compound and BBAL in accordance with the present invention may be used at any cycle of a stepwise peptide synthesis in the same manner as other $N^\alpha$-Boc amino acids. The trifunctional compound or BBAL side chain in the resulting peptide will react selectively with sulfhydryl groups to form thioether cross-links with (a) itself, yielding cyclic peptidic molecules or linear polymers, or (b) other molecules or surfaces, forming various conjugates or biospecifically modified surfaces. This invention provides a means for synthesizing peptides that have a cross-linking handle at any selected locus for the purpose of preparing structurally peptide-based components of biological activity modifiers (e.g. immunogens, immunizing epitopes, vaccines, inhibitors), bioassay and affinity separation materials, and medical prostheses.

The synthesis of a preferred example of the trifunctional compounds of the present invention, BBAL, is accomplished in three stages as shown in Schemes I and II. First, N-bromoacetyl-β-alanine is prepared by a procedure similar to the ones reported by Yamada et al. (Yamada, H. et al, (1984) Nature of the binding site around and reactivity of histidine-15 in lysozyme. *J. Biochem.* 95, 503–510) and Zaitsu et al (Zaitsu, K. et al, (1987) New heterobifunctional cross-linking reagents for protein conjugation, N-(bromoacetamido-n-alkanoyloxy)succinimides. *Chem. Pharm. Bull.* 35,1991–1997) (Scheme I, first reaction). The product is adequately separated from bromoacetic acid, resulting from hydrolysis of excess bromoacetyl bromide, by a series of extractions that obviated the need for an adsorption chromatography step. The product is purified by two crystallizations from ethyl acetate-hexane, rather than from tetrahydrofuran-isopropyl ether, and gave a melting point about 10° C. higher than that reported by Yamada et al (Yamada et al, supra). This acid is converted to its N-hydroxysuccinimide active ester, SBAP, (Scheme I, second reaction) by a technically facile approach whereby the product itself is crystallized from the reaction mixture rather than a urea by-product. Coupling is accomplished with N,N'-diisopropylcarbodiimide in 2-propanol instead of with DCC in a less polar solvent as is commonly done. The synthesis of BBAL is carried out conveniently and cleanly with SBAP and commercially available $N^\epsilon$-Boc-L-lysine (Scheme II). BBAL is a white powder which is readily stored, weighed and used with a peptide synthesizer programmed for $N^d$-Boc amino acid derivatives.

Scheme I

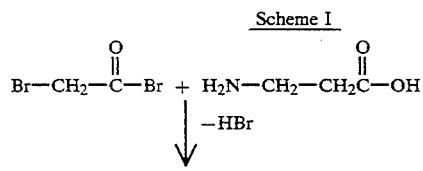

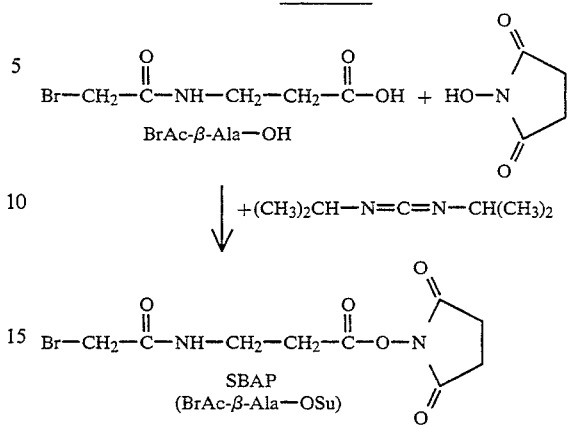

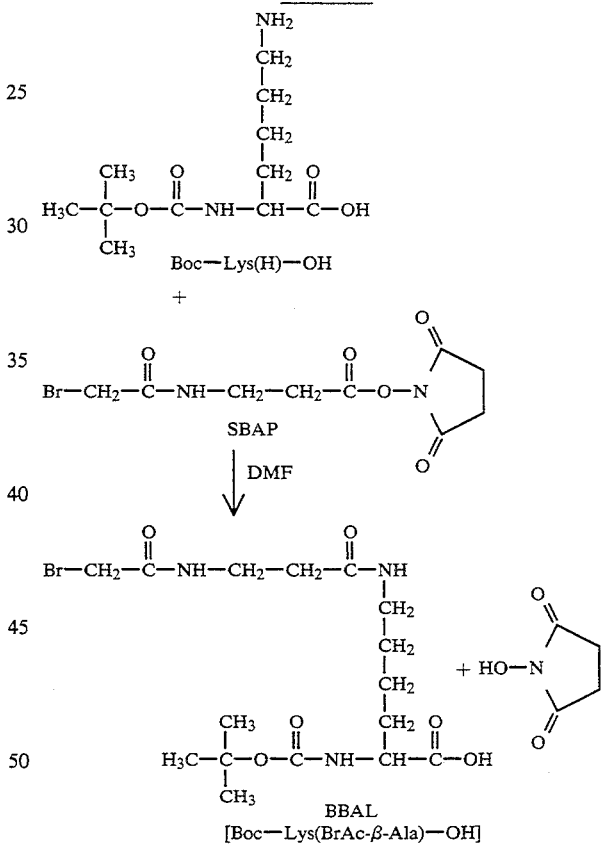

During the course of developing the above synthesis, alternative reagents and solvents were tried. Preliminary examination of products by NMR or MS often revealed significant exchange of Br with Cl in the bromoacetyl moiety whenever Cl was present in the system. This problem was especially severe when bromoacetyl chloride was used, and extractions were conducted over aqueous NaCl, suggesting an ionic mechanism for the halogen exchange. All Cl-containing reagents were then eliminated from use except 1,2-dichloroethane used to crystallize BBAL, since it and dichloromethane were the only solvents that we found from which the final solidification and purification of BBAL could be achieved. The Cl content of BBAL, one time crystallized from dichloroethane, was only 0.38%, but it increased to 1.1% following recrystallization from the same solvent.

A simpler analogue of BBAL, $N^\alpha$-tert-butoxycarbonyl-$N^\epsilon$-bromoacetyl-L-lysine, was prepared by three different routes, each leading to a non-crystallizable, vitreous product. The method deemed most satisfactory for yielding a pure product was the one that paralleled the BBAL synthesis reported above wherein SBAP was substituted with N-succinimidyl bromoacetate, prepared as described by Bernalowicz and Matsueda (Bernatowicz, M. S. et al, (1986) *Anal. Biochem.* 155, 95–102, supra).

The present invention is also directed to methods for preparing synthetic peptide analogs. For polymerizing peptides containing the trifunctional compound BBAL, generally, a cysteine residue or other -SH-containing nucleophile should be also part of the same peptide if cyclization is to occur at pH 6 to about 8 or 9. Above these pH's, a free amino group or other nucleophilic component could be used. Cyclization can be performed by dissolving the BBAL and -SH-containing peptide in an aqueous buffer at pH 7-9. Typically, a buffer consisting of phosphate or bicarbonate is used. The concentration of the peptide is approximately 1 mg/ml or less. Nonaqueous solvent such as DMF, DMSO or methanol could be used alone or with water along with an appropriate proton scavenger such as triethylamine or diisopropylethylamine. The cyclized peptide is purified using high performance liquid chromatography (hplc) and often times the cyclized peptide will elute earlier than the uncyclized precursor. This is due to the diminished available hydrophobic surface area in the cyclized peptide which minimizes its interaction with the reversed phase matrix. The cyclization is performed for anywhere from 15 min. to 24 hrs. depending on the specific conditions used. These include temperature (typically room temperature), solvent, peptide composition and solubility of the peptide. The cyclization reaction is generally followed with hplc and with Ellman's reagent which allows one to monitor the amount of free sulfhydryl group being consumed.

For polymerizing peptides, the same reaction conditions as stated above are used with one exception that the concentration of starting peptide is typically 10–50 mg/ml. Often the peptides are not soluble at these high concentrations but the reaction is allowed to continue regardless of the observed polymerization. After polymerization, the high molecular weight polymers are obtained by dialysis of the reaction mixture against water followed by lyophilizing the dialysate.

For conjugating trifunctional compound and BBAL peptides to any material, it is necessary to react the peptide with an SH group which is a part of the material being conjugated and the solvents and pH's are essentially the same as mentioned above for cyclizing peptides. Examples of such materials include adjuvants, sugars, peptides, lipids, proteins, functional group-bearing polymers, ceramics, glasses and silicas. Conjugating to proteins can be accomplished as detailed by Linder W. and Robey, F. A., supra and by Kolodny N. and Robey, F. A., supra or any other way that provides a free -SH group through either cysteine or other. For example, there are several silane-derivatized materials that contain a free SH group on them and these can be covalently attached to glass surfaces. These allow the basic component of the glass to then react with a BBAL-containing peptide and the result is a thioether linkage between the glass surface and the peptide.

In other examples, 2-iminothiolane, succinimidyl 3-(2-pyridyldithio)propionate (SPDP), and S-acetylmercaptosuccinic anhydride (SAMSA) can be used to introduce the free sulfhydroyl groups at the position of any material where there is a free amino group. The free amino group reacts with these to give a material that contains a free sulfhydryl group which can then be used to react with the BBAL-containing peptides. This procedure for using 2-iminothiolane is outlined in the above-cited reference by Linder and Robey using the N-chloroacetyl chemistries for peptides modified at the amino termini. The above are only examples and those well-versed in the art can modify the above examples for introducing reactive SH groups into materials, organic or inorganic for use in reacting the BBAL or BBAL-containing materials.

The reaction of BBAL-containing peptides is strictly pH dependent; at pH's below 7 the reaction is slowed as the pH is lowered and, as such, the products can be controlled by controlling the pH.

These and other objects of the invention are accomplished by providing a method for the preparation of peptides containing a trifunctional compound such as BBAL which includes the steps of coupling the trifunctional compound or BBAL onto a resin or amino acid or amino acid derivative to form an amide linkage between the amino acid or lysine backbone of the trifunctional compound or BBAL and the fully protected peptide and then deprotecting the fully protected peptide while still preserving the presence of the bromoacetyl or chloroacetyl group on the peptide.

Any peptide can be derivatized using the present method. If the goal is polymerization or cyclization of the modified peptide, a cysteine is placed on the peptide in addition to the trifunctional compound or BBAL.

The BBAL-peptides can be prepared by a procedure which includes forming a symmetric anhydride of BBAL or an active ester of, for example, N-hydroxybenzotriazole (HOBT), reacting the anhydride or ester with an N-terminus of a peptide being synthesized at any position along the way, to form an amide linkage, and deprotecting the peptide with anhydrous hydrogen fluoride or any other similar acid.

The formation of the anhydride or ester is conducted at or about 10° C. to about 30° C., preferably about 25° C.

The reaction of the BBAL-HOBT ester or BBAL symmetric anhydride is conducted at or about 0° C. to about 30° C., preferably 25° C.

The treatment with hydrogen fluoride is conducted at about −5° C/ to about 5° C., preferably 0° C. This treatment occurs for about 10 minutes to about 3 hours, preferably about 2 hours.

BBAL and the other trifunctional compounds can be used effectively in strategies for polymerizing a great variety of synthetic peptides. For example, the peptides can be polymerized "tail-to-tail" if both cysteine and BBAL have been placed in the C-terminal region of the peptide monomers, and they are subjected to conditions that favor reaction of a thiol group of one molecule with a bromoacetyl moiety on another one, etc. The monomer peptides are thus joined through stable thioether linkages. The result of one such experiment is shown by the SDS-PAGE run presented in FIG. 1 which is a SDS-PAGE run of a peptide polymer obtained by intermolecular cross-linking of a BBAL-containing peptide with itself through a coexisting cysteine residue. Lane A shows the molecular weight standards; Lane B shows the synthetic peptide polymer having the monomer sequence, Lys-Ser-Ile-Arg-Ile-Gln-Arg-Gly-Pro-Gly-Arg-Val-Ile-Tyr-Cys-BBAL-NH$_2$ (SEQ. I.D. NO.: 1). The gel was stained with Coomassie Brilliant Blue R250. Molecular weights as high as 30 kDa or more are observable in the mixture of polymer sizes. Other peptides have been polymerized in like manner to yield polymer components with molecular weights exceeding 30 kDa. In general, the size distribution of the peptide polymers depends in part on the solubility and size of the peptide monomers; the greater the solubility, the higher the degree of polymerization..

There appears to be a tendency for peptides to cyclize that have 4 to 6 amino acid residues between the bromoacetyl-bearing and Cys residues. Therefore, it is preferred for optimal polymerization (greatest number of repeat units) to use peptide monomers with more than 6 interstitial residues, more preferably ones with 15 to 20 such residues.

Figure 2:
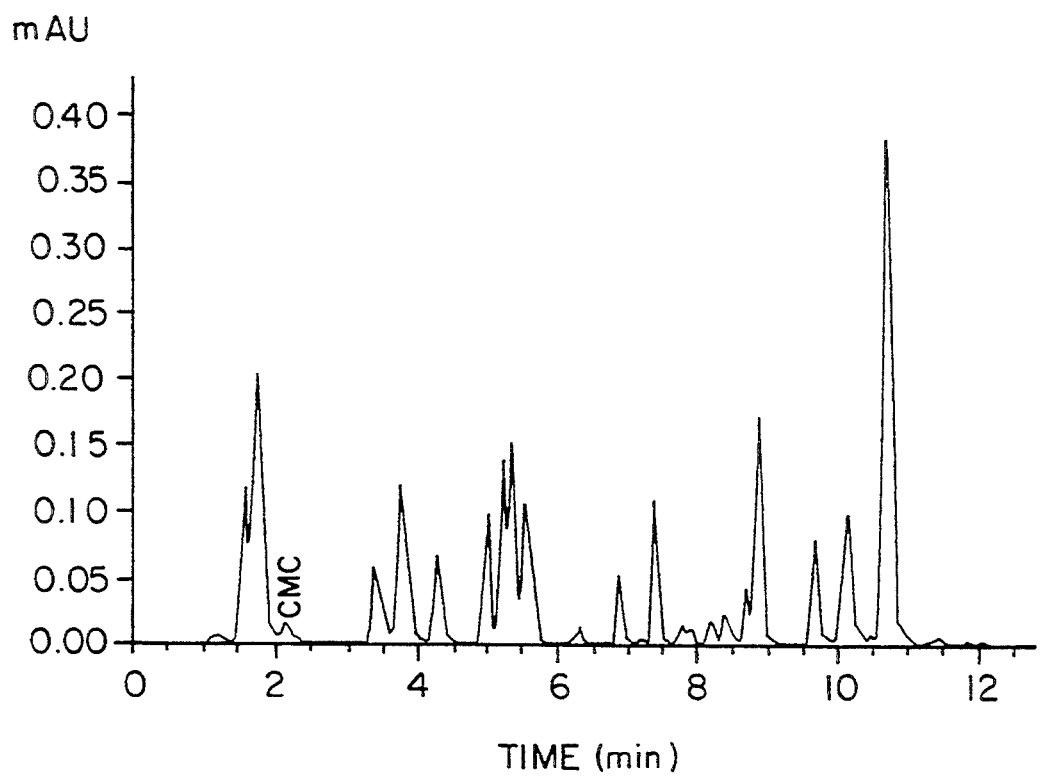
FIG. 2 is a chromatogram of the acid hydrolyzate of the conjugate (Gly-Arg-Gly-Glu-Pro-Thr-BBAL)$_n$-BSA (SEQ I.D. No.: 2.

Synthetic peptides containing BBAL, but not cysteine, are readily conjugated with carriers bearing reactive sulfhydryl groups. Peptide carrier conjugates are commonly used as immunogens or test antigens. We have employed BSA as a carrier following reduction of some of its cystine disulfide bonds with Bu$_3$P in order to release multiple thiol groups as conjugation sites (see Examples below and Kolodny and Robey, supra). Two systems of amino acid analysis were used in this study to evaluate the number of BBAL peptides conjugated to modified BSA. The "PICOTAG" (registered trademark) chromatogram of FIG. 2 clearly shows a measurable amount of CMC from the hydrolysis of Gly-Arg-Gly-Glu-Pro-Thr-BBAL (SEQ. I.D. NO.: 2) linked to reduced BSA. FIG. 2 is a PICOTAG chromatogram of the acid hydrolyzate of the conjugate, (Gly-Arg-Gly-Glu-Pro-Thr-BBAL)$_n$-BSA (SEQ. I.D. NO.: 2). The conjugate was formed by reaction of the BBAL peptide with Bu$_3$P-reduced BSA as detailed under Experimental Procedures and Kolodny and Robey, supra. CMC is cleanly resolved, allowing the sensitive measurement of BBAL peptide covalently coupled to BSA. β-Alanine, which also results from hydrolysis of the conjugate, overlaps the histidine peak and therefore cannot be assayed using the standard conditions for analysis in the PICOTAG system. The amino acid standard chromatogram containing CMC in the PICOTAG system and the calculation to quantify the CMC were presented previously (Kolodny, N. and Robey. F. A., supra).

The PICOTAG amino acid analysis system could not be used to quantify the β-alanine that is also formed from the acid hydrolysis of BBAL-peptide-derived structures. β-Alanine elutes at the same position as histidine (approximately 4.2–4.5 min), and thus the two components cannot be distinguished. A value for β-alanine could be obtained by PICOTAG if the sample undergoing analysis contained no histidine.

Figure 3:
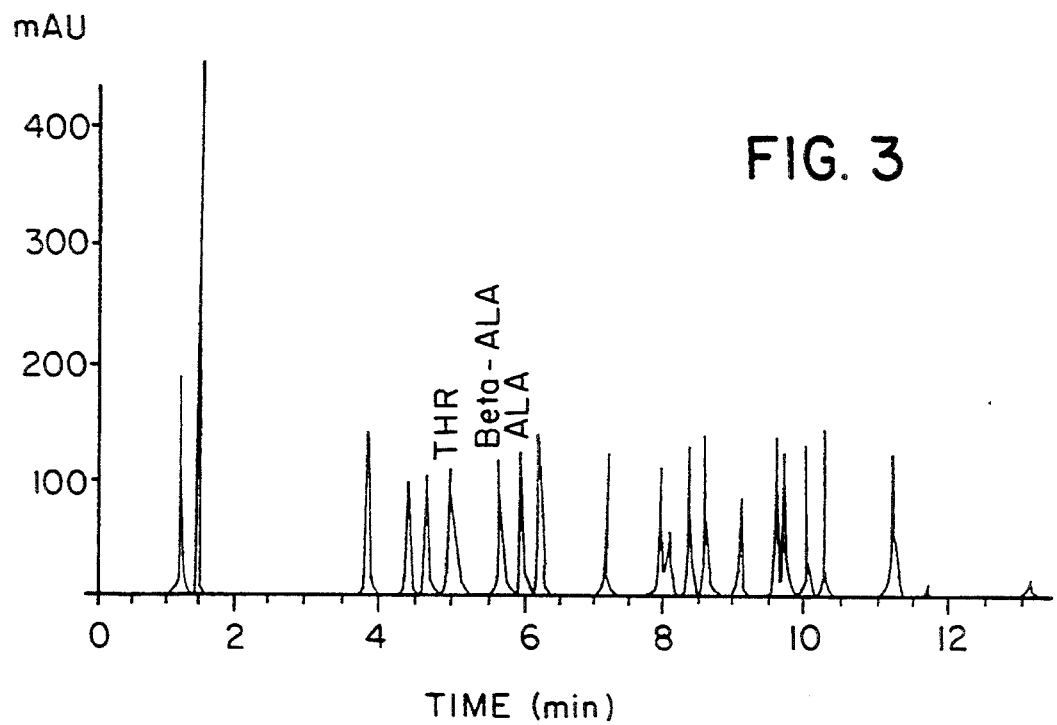
FIG. 3 is a chromatogram for a 1-nmol amino acid standard, spiked with $\beta$-alanine, using the AMINO QUANT system.
Figure 4:
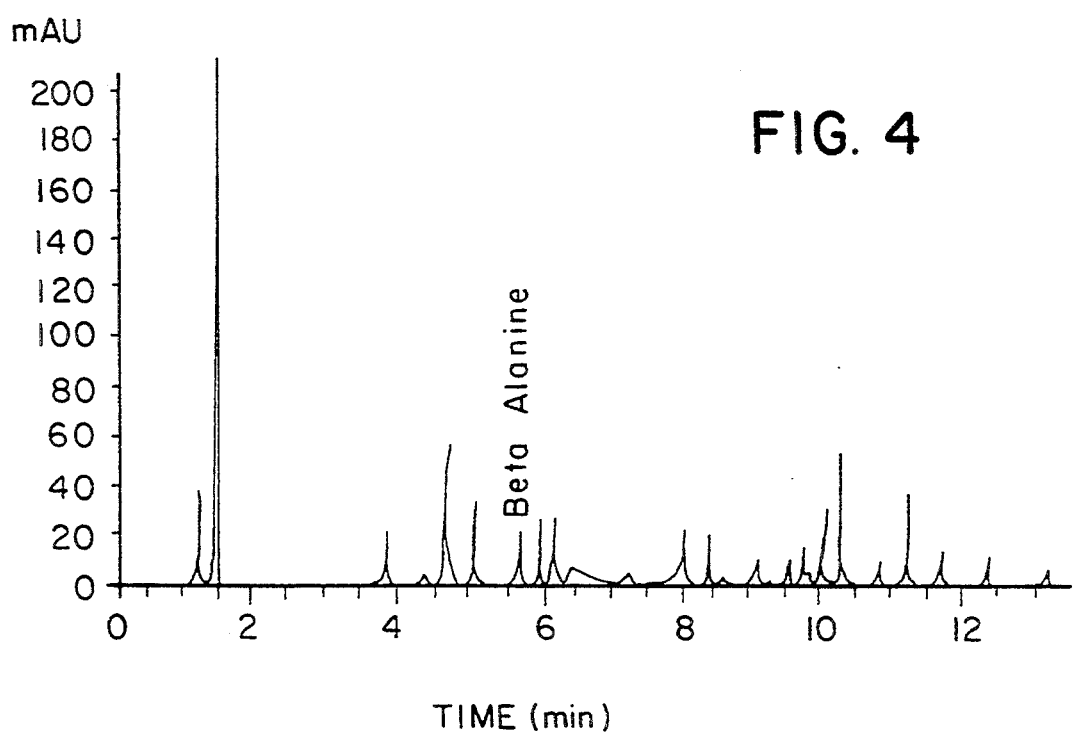
FIG. 4 is an AMINO QUANT analysis of the acid hydrolyzate from the same peptide-BSA conjugate described with respect to FIG. 2.

The second amino acid analysis system that we employed was "AMINO QUANT" (registered trademark). The 1-nmol standard chromatogram, containing 1 nmol of β-alanine, shown in FIG. 3 is a chromatogram for a 1-nmol amino acid standard, spiked with β-alanine, using the AMINO QUANT system. β-Alanine is cleanly resolved from the adjacent amino acids, Thr and Ala, and, thus, is used to quantitate directly the amount of BBAL-containing peptide conjugated to a protein. The naturally occurring amino acids from the carrier protein are likely to mask all other amino acids in the synthetic peptide. CMC, readily detected with the PICOTAG system, cannot be measured from a typical AMINO QUANT run because it elutes with the acidic amino acids. It is clear from examining this chromatogram that the β-alanine peak (designated Beta-ALA) is completely resolved from the nearest amino acids (threonine and alanine). Shown in FIG. 4 is the AMINO QUANT chromatogram of the acid hydrolyzate of the same peptide-BSA conjugate described in FIG. 2. Again, the β-alanine peak is cleanly baseline-resolved from the other amino acids. Thus, FIG. 4 demonstrates the unique versatility of conjugating peptides to cysteine residues of a protein carrier; more than one amino acid marker can be used to quantify the amount of peptide coupled to the carrier protein.

EXAMPLES

Materials and Methods.

Reagent grade chemicals and solvents used in the synthesis were obtained from Fisher Scientific (Pittsburgh, Pa.). β-Alanine and N-hydroxysuccinimide were purchased from Sigma Chemical Company (St. Louis, Mo.). The latter reagent was recrystallized once from ethyl acetate. N,N'-diisopropylcarbodiimide was obtained from Aldrich Chemical Company (Milwaukee, Wis.); bromoacetyl bromide was ordered from Fluka (Ronkonkoma, N.Y.); N$^α$-Boc-L-lysine was obtained from Vega Biochemicals (Tucson, Ariz.).

With the exception of BBAL, all reagents used for the automated synthesis of peptides were purchased from Applied Biosystems, Inc. (Foster City, Calif.). Sodium dodecylsulfate polyacrylamide gel electrophoresis (SDS-PAGE) was performed on the peptide polymers with the gel electrophoresis system sold by Novex (Encinitas, Calif.). This system provided the materials required to run gels by the method of Laemmli (Laemmli, U. K. (1970) Cleavage of structural proteins during the assembly of the head of bacteriophage T4. Nature 227, 680–685). Two amino acid analysis systems were used as described by the manufacturers for the analyses of products that were made using BBAL: "AMINO QUANT" (registered trademark) by Hewlett Packard, Inc. (Gaithersburg, Md.), and "PICOTAG" (registered trademark) by Waters Associates (Millipore Corp., Milford, Mass.). CMC and bovine serum albumin (BSA) were from Sigma Chemical Company and tri-n-butylphosphine (Bu$_3$P) was purchased from Aldrich Chemical Company.

NMR spectra for $^1$H and $^{13}$C were obtained on a Varian XL200 spectrometer at 200 and 50 MHz, respectively. Typically, solutions of 10 mM concentration yielded spectra after the collection of 64 free induction decays for $^1$H (digital resolution of 0.3 Hz) and 60,000 free induction decays for $^{13}$C (digital resolution of 1 Hz). Assignments were based on published spectra and known substituent effects (Kalinowski, H. O. et al, (1988) Carbon-13 NMR Spectroscopy. John Wiley & Sons, New York).

N-Bromoacetyl-β-alanine.

A solution of β-alanine (53.5 g, 0.60 mol) in 600 mL of water was cooled to 5° C. with an ice-alcohol bath. Bromoacetyl bromide (60.0 mL as 95% pure, 0.66 mol) was added under efficient stirring at such a rate as to maintain the temperature below 12° C. Concurrently, 5M NaOH was added at a rate needed to keep the pH near 7. These conditions were maintained for 45 min after completing addition of the bromoacetyl bromide.

Because the latter reagent is a highly toxic irritant, the above operation was carried out in a hood. The pH of the reaction mixture was then adjusted to 1.9–2.0 using 48% HBr and its volume was reduced in a rotary evaporator to approximately 150 mL using a 60° C. bath and aspirator vacuum. The heavy precipitate of NaBr was removed by suction filtration and washed with approximately 15 mL of water.

The filtrate was treated with a small volume of water to dissolve newly precipitated NaBr and then shaken once with hexane-ethyl ether 1:1 v+v (450 mL), once with ethyl ether (450 mL), and 4 times with ethyl acetate-ethyl ether 1:5 v+v (450 mL each time). The first upper phase (rich in bromoacetic acid) and final lower phase were discarded. The next 5 upper phases were pooled, filtered through Whatman #1 paper, and rotary evaporated to remove solvent.

The residue was dried under vacuum and crystallized from hot ethyl acetate (81 mL) by additon of hexane (about 12 mL) and cooling to 4° C. The dried product (31.4 g) was similarly recrystallized from ethyl acetate (69 mL) plus hexane (15 mL) and dried under vacuum/CaCl$_2$. Yield, 30.0 g (23.8 % of theory); mp 88.5°–91° C. [lit. 80°–81° C.]; $^1$H NMR (DMSO-d$_6$) $\delta$2.43 ppm (t, 2H, $\alpha$), 3.26 (q, 2H, $\beta$), 3.84 (s, 2H, $\alpha'$), 8.32 (br, NH), 12.20 (br, COOH); $^{13}$C NMR (DMSO-d$_6$) $\delta$29.31 ($\alpha'$), 33.4 ($\alpha$), 35.2 ($\beta$), 165.91 (Ac C=O), 172.6 (Ala C=O). Anal. Calcd for C$_5$H$_8$BrNO$_3$:C, 28.59; H, 3.84; N, 6.67; Br, 38.05. Found: C, 28.67; H, 3.97; N, 6.64; Br, 38.40.

Succinimidyl 3- (bromoacetamido) propionate (SBAP). To a solution of N-bromoacetyl-$\beta$-alanine (21.00 g, 100 mol) and N-hydroxysuccinimide (13.01 g, 113 mmol) in 2-propanol (280 mL) at room temperature was added 1,3-diisopropyl-carbodiimide (16.0 mL, 101 mmol). After 8–10 min, oily precipitation of the product began, and the walls of the container were scratched to induce crystallization. The mixture was allowed to stand 1 h at room temperature and overnight at 4° C. The crystals were collected, washed with 2-propanol (30 mL), and redissolved in 2-propanol (200 mL brought to reflux). After an overnight stand at 4° C., the crystals were collected, washed with 2-propanol then hexane, and dried under vacuum/CaCl$_2$. Yield, 22.9 g (74.6 % of theory) mp 107°–110.5° C. [lit. (23) 104°–106° C.]; $^1$H NMR (DMSO-d$_6$) $\delta$2.80 ppm (s, 4H, $\alpha''$), 2.82 (t, 2H, $\alpha$), 3.64 (q, 2H, $\beta$), 3.82 (s, 2H, $\alpha'$), 7.03 (br, NH; $^{13}$C NMR (CDCl$_3$), $\delta$25.62 ($\alpha''$), 28.67 ($\beta$), 31.39 ($\alpha$), 35.65 ($\beta$), 166.20 (Ac C=O), 167.30,169.06 (C=O, s). Anal. Cald for C$_9$H$_{11}$BrN$_2$O$_5$: C, 35.20; H, 3.61; N, 9.12; Br, 26.02. Found: C., 35.74; H 3.83; N, 9.20; Br, 26.12.

N$^\alpha$-tert-butoxycarbonyl-N$^\epsilon$-(N-bromoacetyl-$\beta$-alanyl) -L-lysine (BBAL). N$^\alpha$-Boc-L-lysine (17.73 g, 72 mmol) was ground to a fine powder and suspended in N,N-dimethylformamide (DMF) (600 mL). SBAP (18.43 g, 60.0 mmol) was added to the suspension in 5 portions at 10-min intervals. The reaction mixture was stirred for 2 h at room temperature, allowed to stand overnight at 4° C., filtered, and rotary evaporated to remove DMF (bath 30° C., pump vacuum). The residue was shaken with a mixture of ethyl acetate (960 mL), 1-butanol (240 mL) and aq 0.2M KHS04 (300 mL). The upper phase was shaken twice with 0.2 M KHS04 (300 and 150 mL, respectively), filtered (Whatman #1 paper), and rotary evaporated to remove solvent (32° C. bath, pump vacuum). Vacuum was applied (for at least 2 h) to purge last traces of solvent. The oily residue was dissolved in 1,2-dichloroethane (DCE) (400 mL) by gentle warming and swirling. The solution was slowly cooled to 15°–20° C. during which time the product initially precipitated as an oil but was induced to crystallize by scratching. After an overnight stand (4° C.), the product was collected, washed (3×36-mL portions of DCE), and dried in vacuum/CaCl$_2$. Yield, 17.3 g (65.8% of theory); mp 117–122 OC. (decomp); $^1$H NMR (DMSO-d$_6$), $\delta$1.34 ppm (s, 9H,$\alpha'''$), 1.5 (m, 6H, $\beta$, $\gamma$, $\delta$), 2.22 (1, 2H, $\alpha'$), 3.02 (q, imp), 3.50 (m, $\epsilon$, $\beta'$, imp), 3.82 (s+m, $\alpha$+$\alpha'$+imp's), 6.95 (d, Lys-$\alpha$-NH), 7.82 (t, NH), 8.24 (t, NH); $^{13}$C NMR (DMSO-d$_6$) $\delta$22.96 ($\gamma$), 28.13 (CH$_3$), 28.60 ($\beta$), 29.40 ($\alpha''$), 30.41 ($\alpha'$), 34.80 ($\delta$), 35.75 ($\beta'$), 38.17 ($\epsilon$), 53.36 ($\alpha$), 61.32 (imp, HOCH$_2$CON), 77.90 [OC(CH$_3$)$_3$, 155.50 (carbamate C=O), 165.81 (BrCH$_2$C=O), 169.83,174.08 (C=O's). Anal. Calcd for C$_{16}$H$_{28}$BrN$_3$O$_6$: C, 43.84; H, 6.44; N, 9.59; Br, 18.23; Cl, O. Found: C, 43.79; H, 6.61; N, 9.51; Br, 18.32; Cl, 0.38.

Synthesis of BBAL-Containing Peptides.

The various BBAL-containing peptides were synthesized using an automated solid-phase peptide synthesizer (Model 430A, Applied Biosystems, Inc., Foster City, Calif.) that is based on the original Boc/Bzl solid-phase peptide synthesis procedures described in 1963 by R. B. Merrifield (Merrifield, R. B. (1963) Solid phase peptide synthesis. 1. The synthesis of a tetrapeptide. J. Amer. Chem. Soc. 85, 2149–2154). For introducing BBAL residues into peptides at any desired position along the chain, the same double coupling cycles for asparagine that are pre-programmed into the instrument were found to be most suitable when peptides were synthesized on a 0.5-mmol scale, the larger of the two scales that are preprogrammed for the Model 430A. The reason for this is that BBAL is very soluble in DMF, but spraringly soluble in CH$_2$Cl$_2$, and the asparagine coupling steps of the Model 430A employ 1-hydroxybenzotriazole (HOBt) ester formation in DMF.

Briefly, the synthesis first involved the following: A mixture of BBAL and HOBt was made by dissolving 2.0 mmol BBAL in a solution containing 2.0 mmol HOBt in 4.0 mL DMF and 0.3 mL CH$_2$Cl$_2$, The BBAL-HOBt mixture was added to 4.0 mL of 0.5 M N,N'-dicyclohexylcarbodiimide (DCC) in CH$_2$Cl$_2$. This mixture was agitated by bubbling with N$_2$ over a period of at least 30 min at 25° C. The dicyclohexylurea by-product, which precipitated during the formation of the BBAL-OBt ester, was filtered off, and the ester in the filtrate was reacted with a free amine on the PAM resin to give the BBAL-PAM-coupled product. t-Boc was removed from the coupled BBAL in the next cycle with TFA in CH$_2$Cl$_2$ using the manufacturers pre-programmed protocol.

Following the synthesis, the peptide was deprotected and released from the PAM resin using a standard. HF deprotection method as described by Robey and Fields (Robey, F. A., and Fields, R. L. (1989), supra) for preparing bromoacetyl-containing peptides. The only scavenger used was anisole. As mentioned previously (Robey, F. A., and Fields, R. L. (1989), supra), sulfur-containing scavengers such as thiophenol or thioanisole were avoided as a precautionary measure.

Synthesis of Peptide Polymers Using BBAL.

Peptide polymers prepared with the use of BBAL have been synthesized as candidate immunogens. These polymerized peptides were all assembled by following the same procedure detailed previously for making peptide polymers coupled head-to-tail with cysteine at the peptide's C-terminus and bromoacetyl at the N-terminus(18). For polymers involving the use of synthetic peptides containing BBAL, the peptide is designed to contain cysteine at any desired position and BBAL at any other position. The BBAL, Cys-containing peptide was dissolved in 0.5M phosphate buffer, pH 7.2, at a concentration of 20 mg/mL. The polymer was formed generally within 3 h at ambient temperatures, but we routinely allowed the mixture to stir overnight. The mixture was then dialyzed and lyophilized as detailed previously (Robey, F. A., and Fields, R. L. (1989), supra).

Coupling BBAL-Containing Peptides to Bovine Serum Albumin (BSA).

Synthetic peptides were coupled to BSA following the same procedure outlined by Kolodny and Robey (Kolodny, N. et al, supra) for coupling N-terminal bromoacetyl peptides to BSA: To 30 mg BSA dissolved in 5 mL of 0.1M $NaHCO_3$ were added 0.2 mL of a 0.7M solution of $Bu_3P$ in 2-propanol, and the reaction mixture was stirred for 30 min at room temperature. Then, 30 mg of the BBAL-containing peptide was added, and the reaction mixture was continuously stirred for 1 h. The entire 6 mL of the conjugation reaction mixture was dialyzed for 12 h at 4° C. against a 6-L batch of 0.1M $NH_4HCO_3$ and then against 3 changes of the same solution over a 2-day period. The conjugates were then obtained in powder form by lyophilization.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

---

What is claimed:

1. A compound comprising a moiety of the formula $N^\alpha$-tert-butoxycarbonyl-$N^\alpha$-(N-bromoacetyl-$\beta$-alanyl)-L-lysine and further comprising a peptide moiety.

2. A trifunctional compound comprising:
   (a) a haloacetyl or other haloacyl functional group;
   (b) an un-ionized carboxyl group, carboxylate salt, carboxylic acid active ester, acyl halide, symmetrical anhydride or mixed anhydride;
   (c) a protected primary or secondary amine, wherein the protecting group is removable; and
   (d) a peptide moiety.

3. A compound of the formula $N^\alpha$-tert-butoxycarbonyl-$N^\alpha$-N-bromoacetyl-$\beta$-alanyl)-L-lysine, further comprising a material conjugated thereto, wherein said material is selected from the group consisting of peptides, sugars, lipids, proteins.

4. A trifunctional compound comprising:
   (a) a haloacetyl or other haloacyl functional group;
   (b) an un-ionized carboxyl group, carboxylate salt, carboxylic acid active ester, acyl halide, symmetrical anhydride or mixed anhydride;
   (c) a protected primary or secondary amine, wherein the protecting group is removable; and further comprising a material conjugated thereto, wherein said material is selected from the group consisting of peptides, sugars, lipids, and proteins.

5. A compound of the formula $N^\alpha$-tert-butoxycarbonyl-$N^\alpha$-(N-bromoacetyl-$\beta$-alanyl)-L-lysine, further comprising a material conjugated thereto, wherein said material is selected from the group consisting of ceramics, glasses and silicas.

6. A trifunctional compound comprising:
   (a) a haloacetyl or other haloacyl functional group;
   (b) an un-ionized carboxyl group, carboxylate salt, carboxylic acid active ester, acyl halide, symmetrical anhydride or mixed anhydride;
   (c) a protected primary or secondary amine, wherein the protecting group is removable; and further comprising a material conjugated thereto, wherein said material is selected from the group consisting of ceramics, glasses and silicas.

7. A compound of the formula $N^\alpha$-tert-butoxycarbonyl-$N^\alpha$-(N-bromoacetyl-$\beta$-alanyl)-L-lysine, further comprising a functional group-bearing polymeric material conjugated thereto.

8. A trifunctional compound comprising:
   (a) a haloacetyl or other haloacyl functional group;
   (b) an un-ionized carboxyl group, carboxylate salt, carboxylic acid active ester, acyl halide, symmetrical anhydride or mixed anhydride;
   (c) a protected primary or secondary amine, wherein the protecting group is removable; and further comprising a functional group-bearing polymeric material conjugated thereto.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
    ( A ) LENGTH: 16 amino acids
    ( B ) TYPE: amino acid
    ( D ) TOPOLOGY: linear ( i i ) MOLECULE TYPE: peptide ( i i i ) HYPOTHETICAL: NO ( v ) FRAGMENT TYPE: internal ( i x ) FEATURE:
    ( A ) NAME/KEY: Modified-site
    ( B ) LOCATION: 16
    ( D ) OTHER INFORMATION: /label=modifiedaa
        / note="BBAL"

( x i ) SEQUENCE DESCRIPTION: SEQ ID NO:1:

Lys Ser Ile Arg Ile Gln Arg Gly Pro Gly Arg Val Ile Tyr Cys Xaa
  1               5                   10                  15

( 2 ) INFORMATION FOR SEQ ID NO:2:

( i ) SEQUENCE CHARACTERISTICS:
    ( A ) LENGTH: 7 amino acids
    ( B ) TYPE: amino acid
    ( D ) TOPOLOGY: linear ( i i ) MOLECULE TYPE: peptide ( i i i ) HYPOTHETICAL: NO ( v ) FRAGMENT TYPE: internal ( i x ) FEATURE:
    ( A ) NAME/KEY: Modified-site
    ( B ) LOCATION: 7
    ( D ) OTHER INFORMATION: /label=modifiedaa
        / note="BBAL"

( x i ) SEQUENCE DESCRIPTION: SEQ ID NO:2:

Gly Arg Gly Glu Pro Thr Xaa
  1               5

( 2 ) INFORMATION FOR SEQ ID NO:3:

( i ) SEQUENCE CHARACTERISTICS:
    ( A ) LENGTH: 5 amino acids

-continued

```
        (B) TYPE: amino acid
        (D) TOPOLOGY: linear (ii) MOLECULE TYPE: peptide (iii) HYPOTHETICAL: NO (v) FRAGMENT TYPE: internal (ix) FEATURE:
        (A) NAME/KEY: peptide
        (B) LOCATION: 1-5
        (D) OTHER INFORMATION: /note="cell adhesion peptide, see pg.
            2 of Specification"

(xi) SEQUENCE DESCRIPTION: SEQ ID NO:3:

Tyr  Ile  Gly  Ser  Arg
    1                     5
```